United States Patent
Sakamoto et al.

(10) Patent No.: US 10,072,250 B2
(45) Date of Patent: Sep. 11, 2018

(54) METHOD FOR MANUFACTURING NON-ENVELOPED VIRUS

(71) Applicant: TAKARA BIO INC., Shiga (JP)

(72) Inventors: Shuhei Sakamoto, Kusatsu (JP); Yasuhiro Kawano, Moriyama (JP); Katsuyuki Dodo, Kusatsu (JP); Tatsuji Enoki, Kyotanabe (JP); Hirofumi Yoshioka, Rittou (JP); Hikaru Takakura, Kyoto (JP); Junichi Mineno, Uji (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 14/900,837

(22) PCT Filed: Jul. 10, 2014

(86) PCT No.: PCT/JP2014/068438
§ 371 (c)(1),
(2) Date: Dec. 22, 2015

(87) PCT Pub. No.: WO2015/005430
PCT Pub. Date: Jan. 15, 2015

(65) Prior Publication Data
US 2016/0152955 A1    Jun. 2, 2016

(30) Foreign Application Priority Data
Jul. 11, 2013   (JP) ................ 2013-145325

(51) Int. Cl.
| C12N 7/00 | (2006.01) |
| C12N 15/86 | (2006.01) |
| C12N 7/02 | (2006.01) |
| C12N 15/867 | (2006.01) |

(52) U.S. Cl.
CPC ...... C12N 7/00 (2013.01); *C12N 2750/14151* (2013.01)

(58) Field of Classification Search
CPC .............. C12N 7/00; C12N 15/86; C12N 2750/14143; C12N 2750/14043; C12N 2750/14122; C12N 2750/14142; C12N 7/02; C12N 2750/14141; C12N 2750/14351; C12N 2800/50; C12N 15/8673; C12N 2750/14352; C12N 2750/14151; C12N 2750/14152
See application file for complete search history.

(56) References Cited

U.S. PATENT DOCUMENTS

| 5,043,357 A | 8/1991 | Hoffler et al. | |
| 2008/0118970 A1* | 5/2008 | Konz, Jr. | C12N 7/00 435/239 |
| 2008/0132688 A1* | 6/2008 | Zhou | A61L 2/0017 530/413 |
| 2009/0275107 A1* | 11/2009 | Lock | A61K 48/0091 435/239 |
| 2011/0027399 A1 | 2/2011 | Shimamoto et al. | |
| 2016/0273058 A1 | 9/2016 | Akashika et al. | |

FOREIGN PATENT DOCUMENTS

| CN | 102205132 | 10/2011 |
| CN | 102260651 | 11/2011 |
| EP | 0 245 949 | 11/1987 |
| EP | 2 871 239 | 5/2015 |
| JP | 63-14702 | 1/1988 |
| JP | 2001-145496 | 5/2001 |
| JP | 2012-529917 | 11/2012 |
| WO | 97/06272 | 2/1997 |
| WO | 97/08298 | 3/1997 |
| WO | 97/17458 | 5/1997 |
| WO | 00/14205 | 3/2000 |
| WO | 02/12455 | 2/2002 |
| WO | 2009/123183 | 10/2009 |
| WO | 2010/148143 | 12/2010 |
| WO | 2011/074564 | 6/2011 |
| WO | 2014/007120 | 1/2014 |

OTHER PUBLICATIONS

Gencoglu MF, Pearson E, Heldt CL. Porcine parvovirus flocculation and removal in the presence of osmolytes. J Biotechnol. Sep. 30, 2014;186:83-90. Avalilable online Jun. 6, 2014.*
Greenhalgh P, Mehta U. Virus Clearance in Your Process from Start to Finish. BioProcessing Journal. vol. 12, Iss. 4. Jul. 1, 2013.*
R dos Santos Coura, NB Nardi. A role for adeno-associated viral vectors in gene therapy. Genetics and Molecular Biology, 31, 1, 1-11 (2008).*
Morenweiser R. Downstream processing of viral vectors and vaccines. Gene Ther. Oct. 2005;12 Suppl 1:S103-10.*
Vandenberghe LH, Xiao R, Lock M, Lin J, Korn M, Wilson JM. Efficient serotype-dependent release of functional vector into the culture medium during adeno-associated virus manufacturing. Hum Gene Ther. Oct. 2010;21(10):1251-7.*
Lock M, Alvira M, Vandenberghe LH, Samanta A, Toelen J, Debyser Z, Wilson JM. Rapid, simple, and versatile manufacturing recombinant adeno-associated viral vectors at scale. Hum Gene Ther. Oct. 2010;21(10):1259-71.*

(Continued)

*Primary Examiner* — Rachel B Gill
(74) *Attorney, Agent, or Firm* — Wenderoth, Lind & Ponack, L.L.P.

(57) ABSTRACT

The present invention provides a method for efficiently manufacturing a non-enveloped virus with high purity without laborious operation by cultivating cells having the ability to produce a non-enveloped virus and bringing the cells and an acidic solution into contact with each other. A non-enveloped virus vector manufactured by the method of the present invention and a composition having the non-enveloped viral vector as an active ingredient are very useful as gene transfer methods in the fields of basic research and clinical application gene therapy.

7 Claims, 5 Drawing Sheets

(56) References Cited

OTHER PUBLICATIONS

Zolotukhin S, Byrne BJ, Mason E, Zolotukhin I, Potter M, Chesnut K, Summerford C, Samulski RJ, Muzyczka N. Recombinant adeno-associated virus purification using novel methods improves infectious titer and yield. Gene Ther. Jun. 1999;6(6):973-85.*

Sokol F, Kuwert E, Wiktor TJ, Hummeler K, Koprowski H. Purification of rabies virus grown in tissue culture. J Virol. Aug. 1968;2(8):836-49*

Schagen FH, Rademaker HJ, Rabelink MJ, van Ormondt H, Fallaux FJ, van der Eb AJ, Hoeben RC. Ammonium sulphate precipitation of recombinant adenovirus from culture medium: an easy method to increase the total virus yield. Gene Ther. Sep. 2000;7(18):1570-4.*

Taylor AC. Responses of cells to pH changes in the medium. J Cell Biol. Nov. 1962;15:201-9.*

Safaiyan F, Kolset SO, Prydz K, Gottfridsson E, Lindahl U, Salmivirta M. Selective effects of sodium chlorate treatment on the sulfation of heparan sulfate. J Biol Chem. Dec. 17, 1999;274(51):36267-73.*

Venkatakrishnan B. Endosomal PH Mediated Structural Transitions in Adenoassociated Viruses . University of Florida, 2012. Doctoral Dissertation.*

International Search Report dated Oct. 14, 2014 in International (PCT) Application No. PCT/JP2014/068438.

International Preliminary Report on Patentability dated Jan. 12, 2016 in International (PCT) Application No. PCT/JP2014/068438.

Extended European Search Report dated Feb. 9, 2017 in corresponding European Application No. 14823074.1.

Yokoyama et al., "Removal of small non-enveloped viruses by nanofiltration", Vox Sanguinis, 86(4):225-229 (2004).

Takimoto et al., "Effect of Hypochlorite-Based Disinfectants on Inactivation of Murine Norovirus and Attempt to Eliminate or Prevent Infection in Mice by Addition to Drinking Water", Exp. Anim., 62(3):237-245 (2013).

Office Action dated Oct. 10, 2017 in Chinese patent application No. 201480039156.9, with English translation.

Office Action dated Jan. 25, 2017 in corresponding Chinese patent application No. 201480039156.9, with English translation.

Office Action dated May 3, 2018 in Chinese Application No. 201480039156.9, with English translation.

Communication pursuant to Article 94(3) EPC dated May 9, 2018 in European Application No. 14823074.1.

* cited by examiner

[Figure 1]

| Lane | Sample |
|---|---|
| M | Molecular-weight marker SDS-PAGE Standard Low Lange (manufactured by Bio-Rad Laboratories, Inc.) From above, 97, 66, 45, 31, 22, 14 kDa |
| P | rAAV vector solution purified by freeze-thaw method (comparative control) |
| 5 | Fraction 5 |
| 6 | Fraction 6 |
| 7 | Fraction 7 |
| 8 | Fraction 8 |
| 9 | Fraction 9 |
| 10 | Fraction 10 |
| B | Partially purified product before ultracentrifugation (4-fold diluted with ACD-A solution) |
| C | Crude extract by ACD-A solution treatment |

[Figure 2]

| Lane | Sample |
|------|--------|
| 1 | Sample to be applied |
| 2 | Flow-through fraction |
| 3 | Wash fraction |
| 4 | Eluate 1 |
| 5 | Eluate 2 |
| 6 | Eluate 3 |
| P | rAAV vector purified by ultracentrifugation |

[Figure 3]

| Lane | Sample |
|---|---|
| M | Molecular Weight Marker (Broad) (manufactured by TAKARA BIO Inc.) From above, 200, 116, 97.2, 66.4, 44.3, 29.0, 20.1, 14.3, 6.5 kDa |
| 1 | Freeze-thaw method, heparin purification (comparative control) |
| 2 | Citrate buffer + 50 mM NaCl treatment, heparin purification |

METHOD FOR MANUFACTURING NON-ENVELOPED VIRUS

TECHNICAL FIELD

The present invention relates to a method of efficiently producing a non-enveloped virus with high purity and with no laborious operation.

BACKGROUND ART

In the field of gene recombination or the field of medicine, for introduction of a gene into cells of mammals including human, physical methods using electoporation or metal microparticles, chemical methods using nucleic acid, polycation, or liposome, and biological methods using vectors for gene transfer wherein viruses are used as the vectors (hereinafter, referred to as viral vectors) have been currently used. The vectors for gene transfer wherein viruses are used as the vectors mean vectors obtained by altering natural viruses so that the viruses can transfer a desired gene or the like into a target, and the development of such vectors has been recently advanced. Vectors prepared by gene recombination technology are usually called recombinant viral vectors. Well-known examples of vectors which the recombinant viral vectors are derived from include viruses with envelopes, for example retrovirus, lentivirus, Sendai virus, and herpes virus, and viruses without envelopes, for example adenovirus, and adeno-associated virus (hereinafter, referred to as AAV).

In particular, AAV can infect a wide variety of cells including human cells, and AAV infects even non-dividing cells in which differentiation terminates, including blood cells, muscle cells, and nerve cells. In addition, since AAV is not pathogenic to human, it has a low risk of adverse effect. The viral particle of AAV is physicochemically stable. For these reasons, AAV has recently attracted attention to utility value as a vector for gene transfer used in gene therapy for the treatment of congenital genetic disease as well as the treatment of cancer or infection.

A method of producing a gene recombinant viral vector usually comprises introducing elements essential for formation of a viral particle in the form of a nucleic acid construct(s) into a cell to produce a cell having the ability to produce a virus (hereinafter, referred to as a virus-producing cell), and culturing the cell to express the elements essential for formation of the viral particle. In general, of the elements essential for formation of the viral particle, the elements that need to be provided in cis and the elements that can be provided in trans are separately introduced into a cell for viral production, thereby production of a wild-type virus and self-replication of a virus in a host infected with the virus are prevented (Patent Literature 1).

Hereinafter, as an example, a gene recombinant viral vector derived from AAV (hereinafter, referred to as rAAV) is specifically explained. An established method of producing the viral vector comprises 1) introduction of a rAAV plasmid in which an ITR placed at each end of the wild-type AAV genome is left and rep and cap genes are removed, 2) introduction of a plasmid for expression of rep and cap genes to provide Rep and Cap proteins in trans, and since AAV needs provision of supplemental elements from a so-called helper virus such as an adenovirus, a herpesvirus, or a vaccinia virus for formation of the infectious viral particle, 3) infection with an adenovirus (Patent Literature 2). In addition, since a vector solution obtained by the above-mentioned method is theoretically contaminated with adenovirus, in order to avoid the adenovirus contamination, a method of producing a vector comprising, instead of the above-mentioned step 3), step 3') introduction of a helper plasmid expressing only elements essential for formation of an AAV viral particle among adenovirus-derived elements (Helper-free system) has been developed (Patent Literature 3).

Virus-producing cells that have accomplished viral production are collected and homogenized to obtain a cell homogenate containing rAAV vectors. The cell homogenate is subjected to a suitable step such as filtration with a filter, ultracentrifugation, chromatography, or ultrafiltration to purify the rAAV vectors as a final product.

At present, as use of viral vectors is extended to the field of basic research or clinical application for gene therapy, a method of obtaining a viral vector with higher titer and higher purity is needed. Various improved methods are disclosed. For example, a method of enhancing viral production and a release rate of the virus into a culture supernatant which comprises culturing a virus-producing cell under a stress condition in which a culture medium has an elevated pH is known (Patent Literature 1). Other methods comprise improvement of steps on and after purification of a produced virus. On the other hand, there is still room for improvement in treatment of a virus-producing cell performed before purification of the virus.

CITATION LIST

Patent Literatures

Patent Literature 1: WO00/14205
Patent Literature 2: WO97/06272
Patent Literature 3: WO97/17458

SUMMARY OF INVENTION

Problems to be Solved by the Invention

An objective of the present invention is to provide a method of efficiently producing a non-enveloped virus with high purity and with no laborious operation.

Solutions to the Problems

The present inventors intently studied for the purpose of providing a method of efficiently producing a non-enveloped virus with high purity and with no laborious operation, and as a result, found that a non-enveloped virus with high purity was efficiently obtained with no laborious operation by culturing a virus-producing cell and bringing the cell into contact with an acidic solution. Thus, the present invention was completed.

The present invention is outlined as follows. The present invention relates to:

[1] A method of producing a non-enveloped virus, the method comprising:
(a) a step of culturing a cell having the ability to produce a non-enveloped virus,
(b) a step of bringing the cell into contact with an acidic solution, and
(c) a step of obtaining the non-enveloped virus;
[2] The method according to [1], wherein the acidic solution is at pH 3.0-6.9;
[3] The method according to [1] or [2], wherein the acidic solution contains a sodium ion and/or a potassium ion,

[4] The method according to any one of [1] to [3], wherein step (c) comprises purifying the non-enveloped virus;

[5] The method according to [4], wherein the purification of the non-enveloped virus is performed by an operation selected from ultracentrifugation, chromatography, and ultrafiltration;

[6] The method according to any one of [1] to [5], wherein the non-enveloped virus is an adeno-associated viral vector; and

[7] The method according to any one of [1] to [6], wherein the acidic solution contains a cation and citric acid.

Effects of the Invention

According to the present invention, a method of efficiently producing a non-enveloped virus with high purity and with no laborious operation is provided. Further, an acidic solution used in the method and a non-enveloped virus produced by the method are provided. A crude extract of virus obtained by using the acidic solution of the present invention can be applied to a conventional method for purifying a non-enveloped virus.

BRIEF DESCRIPTION OF DRAWINGS

FIG. 4-1 A graph showing genomic titer in Example 10.

FIG. 4-2 A graph showing protein concentration (A280) in Example 10.

FIG. 4-3 A graph showing AAV purity in Example 10.

MODE FOR CARRYING OUT THE INVENTION

The non-enveloped virus as used herein refers to a virus other than an enveloped virus. The enveloped virus refers to a virus having a lipid layer or a lipid bilayer on the viral surface. An envelope is formed when a virus passes through a membrane of a nucleus, an endoplasmic reticulum, Golgi apparatus, a plasma membrane, or a cell membrane to bud. The envelope typically involves proteins derived from a host or viral proteins expressing on the host's cell membrane, and plays an important role in infection to a target cell. The non-enveloped virus, as described above, refers to a virus other than the enveloped virus. Representative examples of the non-enveloped virus include DNA genome viruses, for example adenovirus, parvovirus, papovavirus, and human papillomavirus, and RNA genome viruses, for example rotavirus, coxsackie virus, enterovirus, sapovirus, norovirus, poliovirus, echovirus, hepatitis A virus, hepatitis E virus, rhinovirus, and astrovirus.

The non-enveloped virus produced by the production method of the present invention includes, but not limited to, a non-enveloped virus for which a production method has been already known, a non-enveloped virus newly obtained from nature, and recombinant viral vectors derived from the above-mentioned non-enveloped viruses. Preferable examples of the non-enveloped virus produced by the production method of the present invention include adenovirus, and AAV belonging to family Parvoviridae.

The cell having the ability to produce a virus (virus-producing cell) as used herein refers to a cell expressing elements necessary for viral production and producing viral particles. The virus-producing cell used in the production method of the present invention includes, but not limited to, a virus-producing cell obtained from environment or a clinical sample from a patient with an infection, and an artificially prepared virus-producing cell. The artificially prepared virus-producing cell is preferably used in the present invention, and examples thereof include a non-enveloped virus-producing cell prepared by introducing a nucleic acid to provide elements essential for particle formation of a desired non-enveloped virus, and a nucleic acid to be enclosed in the particle of the non-enveloped virus into any cell, and a virus-producing cell prepared by artificially infecting a desired cell with a non-enveloped virus and/or a helper virus necessary for production of the non-enveloped virus.

The viral vector as used herein means both a particle composed of a protein shell referred to as a capsid, that is, a viral particle, and a viral genome (the form of nucleic acid) included in the viral particle. For example, in the case of AAV, a rAAV vector means either a rAAV particle having a capsid or a viral genome DNA present in the rAAV particle. The present invention may be also applied to a virus-like particle (for example, an AAV hollow particle: WO2012/144446). Thus, the aspect of the viral particle includes a virus-like particle and a viral hollow particle.

Hereinafter, as an example, a rAAV vector is explained. Examples of the elements essential for formation of the rAAV particle include (A) AAV-derived Rep and Cap proteins, and (B) adenovirus-derived elements, for example, nucleic acid sequences to provide E1a protein, E1b protein, E2 protein, E4 protein, and VA RNA.

The "any cell" is not particularly limited. Examples of the "any cell" include cells of mammals such as human, monkey, and rodent, and preferable examples thereof include a 293 cell (ATCC CRL-1573), a 293T cell (ATCC CRL-11268), a 293F cell, a 293FT cell (all manufactured by Life Technologies Corp.), a G3T-hi cell (WO06/035829), an Sf9 cell, and commercially available cell lines for viral production, for example an AAV293 cell (manufactured by Stratagene Corp.), which have high transformation efficiency. For example, the 293 cell or the like constantly expresses adenovirus E1 protein. Also, a cell modified to transiently or constantly express one or some of proteins necessary for rAAV production may be used.

Examples of the nucleic acid to provide elements essential for rAAV particle formation include (a) a nucleic acid encoding the Rep protein, a nucleic acid encoding the Cap protein, and (b) a nucleic acid encoding adenovirus-derived elements. The forms of these nucleic acids are not limited. These nucleic acids can be inserted into a plasmid or a viral vector as one or more nucleic acid constructs capable of providing the elements, and then the plasmid or the viral vector can be introduced into the cell. Examples of a nucleic acid construct for (a) include a pRC2-mi342 vector and pHelper vector (manufactured by TAKARA BIO Inc.) which are commercially available plasmids. In the case where a baculovirus vector is used for introduction of nucleic acid constructs for (a) and (b), vectors such as Bac-Rep and Bac-Cap may be used. As used herein, the nucleic acid encoding the Cap protein encodes not only the Cap protein but also an assembly-activating protein (AAP) necessary for formation of an AAV particle in an open reading frame different from that of the encoded Cap protein (Proc. Natl. Acad. Sci. USA, 2010, Vol. 107, pp. 10220-10225). Unless otherwise noted, the "nucleic acid encoding the Cap protein" means a nucleic acid encoding AAP in addition to the Cap protein. When a mutation that destroys the function of AAP (spontaneously or artificially) occurs in the nucleic acid encoding the Cap protein, a nucleic acid encoding AAP may be further introduced into the cell. Regarding (b), since nucleic acids encoding E1a and E1b proteins are inserted and constantly expressed in the genome of a 293 cell or the like, it is not necessary to introduce the nucleic acids into such cells. The nucleic acids encoding E1a and E1b proteins may be introduced depending on the cell used, if necessary.

The nucleic acid to be enclosed in the rAAV particle is composed of ITR sequences derived from AAV and a nucleic acid desired to be carried by a rAAV vector. Examples of the nucleic acid desired to be carried by a rAAV vector include any foreign gene, for example a nucleic acid for providing a polypeptide (enzyme, growth factor, cytokine, receptor, structural protein, etc.), an antisense RNA, a ribozyme, a decoy, an RNA that induces RNA interference, or the like. In addition, for control of expression of the foreign gene, a suitable promoter, enhancer, terminator and other transcriptional regulatory elements may be inserted into the nucleic acid. For example, the nucleic acid to be enclosed in the rAAV particle may contain any foreign gene desired to be carried by the rAAV vector between two ITR sequences, or may contain any foreign gene desired to be carried by the rAAV vector and at least one element for control of expression of the foreign gene between two ITR sequences. The nucleic acid to be enclosed in the viral particle can be introduced as a nucleic acid construct in the form of a plasmid into the cell. The plasmid can be constructed, for example, by use of a pAAV-CMV vector (manufactured by TAKARA BIO Inc.) which is commercially available, or the like.

Examples of a method for introduction of the nucleic acid construct include a transient introduction method and a constant introduction method.

The transient introduction method is not particularly limited, and a known transient introduction method can be used, including a calcium phosphate method, a lipofection method, a DEAF dextran method, a polyethyleneimine method, and an electroporation method. Also, commercially available reagents, for example TransIT (registered trademark)-293 Reagent (manufactured by Mirus Bio LLC), TransIT (registered trademark)-2020 (manufactured by Mirus Bio LLC), Lipofectamine 2000 Reagent (manufactured by Life Technologies Corp.), Lipofectamine 2000CD Reagent (manufactured by Life Technologies Corp.), FuGene (registered trademark) Transfection Reagent (manufactured by Promega Corp.), etc. may be used. An introduction method comprising use of baculovirus and an insect cell may be also used.

The constant introduction method is not particularly limited, and a known constant introduction method can be used, including a method comprising use of a retroviral vector, and a method comprising introduction of a nucleic acid into a cell in the same manner as a transient introduction method for a plasmid and selection of the cell in which the nucleic acid is integrated in the chromosome. For the method comprising use of a retroviral vector, commercially available reagents, for example Retrovirus Constructive System (manufactured by TAKARA BIO Inc.), may be used.

As described above, the rAAV vector is explained as an example. The first step for production of a non-enveloped virus of the present invention comprises culturing the non-enveloped virus-producing cell prepared as described above. The culture of the non-enveloped virus-producing cell can be performed under known culture conditions. Examples of the culture conditions include, but not limited to, culture at a temperature of 30 to 37° C., a humidity of 95%, and a $CO_2$ concentration of 5 to 10%. The cell culture may be performed at a temperature, a humidity and a $CO_2$ concentration out of the above-mentioned ranges, as long as desired cell growth and production of the non-enveloped virus are accomplished. A culture period is not particularly limited. For example, the culture is continued for 12 to 150 hours, preferably 48 to 120 hours. A medium used for culturing the non-enveloped virus-producing cell is not particularly limited as long as the medium contains components necessary for cell culture. Examples of the medium include basic synthetic media, for example DMEM, IMDM, and DMEM: F-12 (all commercially available from Sigma-Aldrich Co. LLC, etc.). These basic synthetic media may further contain fetal bovine serum, growth factors, or peptides, or may contain increased amounts of amino acids, as necessary.

The second step comprises bringing the non-enveloped virus-producing cell cultured as described above into contact with an acidic solution. The second step is performed by suspending pellets of the non-enveloped virus-producing cell in the acidic solution, wherein the pellets are collected by removing a culture solution by centrifugation or filtration after the cell culture, or by adding a component to the culture solution of the non-enveloped virus-producing cell, wherein the component is capable of making the culture solution acidic. At the time of bringing the non-enveloped virus-producing cell into contact with the acidic solution, the non-enveloped virus-producing cell has already accomplished the viral production. During the contact with the acidic solution, the viral production and the cell growth are not observed. Examples of temperature and time for the contact with the acidic solution include, but not particularly limited to, 0 to 40° C., preferably 4 to 37° C., and one minute to 48 hours, preferably 5 minutes to 24 hours. The non-enveloped virus-producing cell can be stored in a state of contact with the acidic solution in an ultra-deep freezer, for example at −80° C., for a long time. This contact step results in the release of the non-enveloped virus outside the producing cell. The method of the present invention may or may not comprise a physical cell disruption method such as ultrasonic disruption or freeze-thaw which is a conventional method.

The acidic solution as used herein refers to a solution showing acidity. The acidic solution of the present invention is not limited as long as the acidic solution shows a lower pH than that of the non-enveloped virus-producing cell being cultured, and not limited as long as a crude extract containing the non-enveloped virus is obtained by treating the non-enveloped virus-producing cell that has accomplished the viral production with the acidic solution. The acidic solution used in the present invention has, for example, a pH of 3.0 to 6.9, preferably a pH of 3.0 to 6.0, more preferably a pH of 3.0 to 5.0. Examples of the acidic solution used in the present invention include solutions containing a compound selected from the group consisting of citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and their salts, and Good's buffers having a buffering region at pH 7 or lower such as MES, and Bis-Tris. In the present invention, an acidic solution containing citric acid, acetic acid, phosphoric acid, or a salt thereof is preferably used. The concentration of the compound contained in the acidic solution is preferably 5 mM to 1 M, more preferably 10 to 500 mM. A solvent for preparing the acidic solution used in the present invention is not particularly limited. The solvent can be appropriately selected from water, buffers, media for cell culture, and the like. The solvent may contain various ions depending on the subsequent operation. Examples of such ions include, but not limited to, cations such as a sodium ion, a potassium ion, and a magnesium ion. Preferable examples of the solvent for the acidic solution used in the present invention include water, an aqueous solution containing a sodium ion, a potassium ion and/or a magnesium ion, such as a sodium chloride solution, a potassium chloride solution, a magnesium chloride solution and a physiological saline, and a solution containing a saccharide such as a glucose solution and a sucrose solution. The sodium ion concentration and/or the potassium ion concentration of the acidic solution is not particularly limited, and it is for example 5 mM to 2.7 M, preferably 5 mM to 1 M, more preferably 20 to 800 mM. These ion concentrations can be appropriately determined depending on the third step as described later. For example, when a crude extract of the non-enveloped virus obtained by use of the acidic solution of the present invention is subjected to chromatography to purify the non-enveloped virus, the acidic solution adjusted to have a suitable salt concentration, for example sodium ion concentration of 3 M or lower, preferably 50 mM to 2 M is preferably used. For example, the acidic solution may be a 30 to 40 mM citrate buffer solution containing 200 to 500 mM sodium ion. The acidic solution may be a 40 to 60 mM citrate buffer solution containing 300 mM to 2.5 M sodium ion.

The component capable of making the culture solution of the non-enveloped virus-producing cell acidic when added to the culture solution is not limited as long as the component changes the pH of the culture solution into a lower pH than that of the non-enveloped virus-producing cell being cultured, and not limited as long as a crude extract containing the non-enveloped virus is obtained from the non-enveloped virus-producing cell that has accomplished the viral production. Examples of the component capable of making the culture solution acidic used in the present invention include citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and their salts, and the same solutions as the acidic solutions described above. The addition amount of the component capable of making the culture solution acidic is not particularly limited as long as a crude extract containing the non-enveloped virus is obtained from the non-enveloped virus-producing cell that has accomplished the viral production, and may be appropriately determined by a person skilled in the art. In addition, various ionic components may be added together with the component capable of making the culture solution acidic. For example, solution of the same ions as those described above for the acidic solution may be used.

The crude extract of the non-enveloped virus released outside the cell obtained through the above described steps is subjected to the third step for obtaining the non-enveloped virus. For example, the crude extract obtained by the second step is subjected to centrifugation or filtration with a filter to obtain a supernatant or a filtrate. Thus a partially purified non-enveloped viral vector is prepared separately from the cells and residues, and thereby the non-enveloped virus is obtained. In the method of the present invention, the partially purified non-enveloped viral vector obtained by the above-described method can be stably stored as it is, or can be stably stored after addition of a neutralizing solution. The neutralizing solution is a solution capable of adjusting the pH of the partially purified non-enveloped viral vector solution to neutral. Examples of the neutralizing solution include, but not particularly limited to, basic solutions such as sodium hydroxide and potassium hydroxide, and highly-concentrated buffers having a pH of 8.5 to 10.0. For example, the partially purified non-enveloped viral vector may be neutralized using a 1 to 3 M Tris-HCl buffer, a TAPS buffer, a Bicine buffer, or a glycine buffer. In the method of the present invention, the partially purified non-enveloped viral vector can be subsequently purified by ultracentrifugation, chromatography, ultrafiltration, or other known methods to obtain a concentrated or purified non-enveloped virus as a final product. The purification of the non-enveloped virus by chromatography can be performed by an ion-exchange column (for example, Mustang Q manufactured by Pall Corp.), an affinity column (for example, AVB Sepharose manufactured by GE Healthcare Ltd., or a heparin column), a hydroxyapatite column, or the like. In addition, the partially purified non-enveloped viral vector or the crude extract obtained by the second step can be treated with a higher concentration of acid to precipitate impurities contained in the partially purified non-enveloped viral vector or the crude extract. The step of treating the partially purified non-enveloped viral vector or the crude extract with the higher concentration of acid comprises, for example, addition of an acidic solution or a component, wherein examples of the acidic solution or the component are the same as those cited as examples of the acidic solution or the component capable of making the culture solution acidic used in the second step. The "higher concentration of acid" is an acid having higher concentration than the acid concentration of the partially purified non-enveloped viral vector or the crude extract obtained by the second step, and is not particularly limited. For example, when a crude extract is obtained by treating the cell with a 30-40 mM citrate buffer solution, citric acid or a citrate buffer solution is added to the crude extract so that the final concentration of citric acid is increased to 50-200 mM, thereby contaminating proteins contained in the crude extract can be precipitated. The virus thus obtained is stored by a suitable method, for example freezing, until before use for a desired purpose.

As used herein, the yield of the non-enveloped virus is shown as a titer of the non-enveloped virus. The titer of the non-enveloped virus is expressed as, but not limited to, in a certain amount of a sample, a) the number of genomes (genomic titer) of the non-enveloped virus, b) the infection ability (infectious titer) of the non-enveloped virus to a cell as determined experimentally, or c) the amount of protein (or the purity of protein) constituting the non-enveloped virus as measured, which is specified as necessary.

Examples of a method for determination of the genomic titer include a method comprising determination of the copy number of the virus genome in a non-enveloped virus-containing sample by PCR.

Examples of a method for determination of the infectious titer include a method comprising infection of a suitable target cell with serially diluted solutions of the non-enveloped virus, and detection of change in the form of the cell (cytopathy), a method comprising detection of the expression of the introduced gene, and a method comprising determination of the copy number of the virus genome introduced into the cell.

Examples of a method for determination of the amount of protein (or the purity of protein) constituting the non-enveloped virus include a method comprising quantitative determination of the protein by an immunological technique.

The method of the present invention is suitably used for non-enveloped viruses having acid resistance including, but not limited to, AAV type 1 to type 6.

According to the present invention, in addition to the method of producing a non-enveloped virus, the acidic solution used in the method, and the non-enveloped virus produced by the method are provided. In addition, a pharmaceutical composition comprising the non-enveloped virus produced by the method of the present invention as an active ingredient is provided. The pharmaceutical composition can be appropriately prepared according to techniques for production of viral formulations for gene therapy. For example, the non-enveloped virus obtained by the production method of the present invention can be further concentrated, purified and processed by known methods, and then formulated into a pharmaceutical composition. The pharmaceutical composition can be used ex vivo for cells from patients, or administered directly to patients.

Another aspect of the present invention provides a kit for producing a non-enveloped virus, which comprises:

a vector comprising a nucleic acid to provide elements essential for particle formation of a non-enveloped virus, a vector comprising a nucleic acid to be enclosed in the particle of the non-enveloped virus, and an acidic solution. The kit may further comprise a neutralizing solution for neutralizing the obtained non-enveloped virus-containing solution.

Further another aspect of the present invention prvides a kit comprising an acidic solution and a neutralizing solution.

Further another aspect of the present invention provides a kit comprising:

an acidic solution,
a neutralizing solution,
a column for purification of virus, and
various buffers for use in column purification.

EXAMPLES

Hereinafter, the present invention is more specifically explained by way of Examples which the present invention is not limited to.

Example 1: Effect of Treatment with Acidic Solution in Step of Preparation of Crude Extract (1) Seeding of Cell for Production of rAAV Vector In DMEM/F12 (manufactured by Gibco Corp.) containing 10% FBS (manufactured by Nichirei Biosciences Inc.), 293 cells were suspended. The suspension was seeded to two 10 cm dishes for cell culture (manufactured by Corning Inc.), and then, cultured overnight in a $CO_2$ incubator at 37° C. The cells were confirmed to be 70% confluent.

(2) Transfection of Plasmid for Production of rAAV Vector

The cells obtained by Example 1-(1) were transfected with each 23.1 μg of a pRC plasmid encoding the Rep protein and the Cap protein of AAV type 2 (hereinafter, referred to as AAV2) (manufactured by Cell Biolabs, Inc.), a pHLP plasmid containing adenovirus-derived E2A, VA and V4 sequences (manufactured by Cell Biolabs, Inc.), and a pAAV-AcGFP plasmid containing "a CMV promoter sequence, a sequence encoding AcGFP1, and a PolyA sequence" as an expression cassette for fluorescent protein AcGFP1 between two ITRs of AAV2. Seven hours after the transfection, the medium was completely removed, and 15 mL/dish of DMEM/F12 was added to the dishes. The cells were cultured in a $CO_2$ incubator at 37° C. for 2 days.

(3) Collection of rAAV Vector-Producing Cell

The medium was completely removed from the dishes obtained by Example 1-(2). Then, 3 mL of PBS (manufactured by Gibco Corp.) containing 20 mM EDTA (manufactured by Wako Pure Chemical Industries, Ltd.) was added to each dish, and reacted at room temperature for several minutes for cell desquamation. Then, a solution containing the cells was collected, and centrifuged at 4° C. and 1,750×g for 10 minutes. A supernatant was removed. A cell pellet was resuspended in 4 mL of PBS. The suspension was put in two centrifuging tubes in an amount of each 2 mL. Each centrifuging tube was centrifuged at 4° C. and 1,750×g for 10 minutes. Then, a supernatant was removed.

(4) Preparation of Crude Extract by Ultrasonic Disruption Method

To one of the centrifuging tubes obtained by Example 1-(3), 1 mL of PBS was added, and the tube was subjected to 5 cycles, each cycle consisting of disruption by an ultrasonic disruption apparatus (manufactured by BM Equipment Co. Ltd.) and pause, to prepare a cell homogenate containing a rAAV vector. The cell homogenate was centrifuged at 4° C. and 14,000×g for 10 minutes. A supernatant was collected to obtain a crude extract of the rAAV vector.

(5) Preparation of Crude Extract by Treatment with Acidic Solution (ACD-A Solution)

To the other centrifuging tube obtained by Example 1-(3), 1 mL of an ACD-A solution (manufactured by TERUMO Corp.) was added, followed by mixing with a vortex mixer for 15 seconds. The mixture was left standing in a water bath at 37° C. for 5 minutes, again mixed by a vortex mixer for 15 seconds, and then centrifuged at 4° C. and 14,000×g for 10 minutes. A supernatant thus obtained was used as a crude extract. The ACD-A solution comprises 2.2 w/v % sodium citrate hydrate, 0.8 w/v % citric acid hydrate, and 2.2 w/v % glucose, and has a pH of 4.5-5.5.

(6) Determination of Genomic Titer and Protein Concentration (A280) of Crude Extract After 2 μL of the crude extracts prepared by Example 1-(4) and Example 1-(5) were 50-fold diluted with DNaseI buffer (manufactured by TAKARA RIO Inc.), the diluted crude extracts were treated with DNaseI (manufactured by TAKARA RIO Inc.) at the concentration indicated in the instructions to remove free genomic DNA and plasmid DNA. After heat treatment at 75° C. for 30 minutes for inactivation of DNaseI, a DNaseI-treated solution containing the rAAV vector was obtained and stored at 4° C. or −20° C. To 100 μL of the DNaseI-treated solution containing the rAAV vector, 100 μL of buffer AL (manufactured by QIAGEN GmbH) was added, and maintained at 56° C. for 10 minutes. The solution was 100-fold diluted with water for injection (manufactured by Otsuka Pharmaceutical Co., Ltd.), and 2 μL of the dilution was used for determination of the genomic titer of the rAAV vector. For determination of genomic titer, SYBR Premix ExTaqII (manufactured by TAKARA BIO Inc) was used, and operations including preparation of a reaction solution etc. followed the instructions attached to the kit. As a standard, a linearized DNA obtained by digestion of a pAAV-AcGFP plasmid with restriction enzyme EcoRI (manufactured by TAKARA BIO Inc.) was used. Primer sequences used in realtime PCR are sequences that anneal to the CMV promoter sequence placed in the AcGFP1 expression cassette. In addition, the protein concentration of the crude extracts prepared by Example 1-(4) and Example 1-(5) was determined as A280 by Nano- Drop1000 (manufactured by Thermo Fisher Scientific Inc.) in a protein measurement mode. These results are shown in Table 1.

TABLE 1

| Extraction condition | Genomic titer ($\times 10^{11}$ VG/mL) | A280 measurement |
|---|---|---|
| Ultrasonic disruption (Comparative control) | 3.6 | 9.40 |
| ACD-A solution treatment | 10.2 | 1.46 |

VG = Vector genome

As seen from Table 1, the genomic titer of the crude extract prepared under the condition of ACD-A solution treatment was 2.8 times higher than that of the crude extract prepared under the condition of ultrasonic disruption. In addition, the A280 measurement of the crude extract prepared under the condition of ACD-A solution treatment was lower than that of the crude extract prepared under the condition of ultrasonic disruption. These results show that the rAAV vector is effectively extracted by the ACD-A solution treatment and the crude extract prepared by the ACD-A solution treatment contains lower amounts of contaminating proteins.

Example 2: Effect of Crude Extraction with Acidic Solution in Purification Step (Purification by Ultracentrifugation)

(1) Production of rAAV Vector and Preparation of Crude Extract with ACD-A Solution A rAAV vector-producing cell was collected in the same manner as Example 1-(1) to (3), except that a CellBIND (registered trademark) 1225 flask (manufactured by Corning Inc.) was used as a culture vessel and associated reaction systems were scaled up. To the collected cell pellet, 10 mL of the ACD-A solution was added, followed by mixing with a vortex mixer for 15 seconds. The mixture was left standing in a water bath at 37° C. for 5 minutes, again mixed by a vortex mixer for 15 seconds, and then centrifuged at 4° C. and 14,000×g for 10 minutes. A supernatant thus obtained was used as a crude extract. As a comparative control, a rAAV vector-producing cell cultured in the same conditions was subjected to a freeze-thaw method, which is a conventional extraction method for rAAV vector, to prepare a crude extract, and the crude extract was treated with BENZONASE (registered trademark) (manufactured by Merck Millipore Corp.) (final concentration: 250 U/mL), and then ultracentrifuged twice to obtain a purified rAAV vector solution.

(2) Partial Purification

The crude extract obtained by Example 2-(1) was centrifuged at 4° C. and 14,000×g for 20 minutes. A supernatant was collected. The collected supernatant was filtered with a posidyne filter having pore size of 0.2 μm (manufactured by Pall Corp.) to obtain a partially purified product.

(3) Purification by Ultracentrifugation

The partially purified product obtained by Example 2-(2) was put in an Ultra-Clear tube (manufactured by Beckman Coulter, Inc.), and purified by a density gradient ultracentrifugation method using cesium chloride by a conventional method.

(4) Collection of Fraction and Measurement of Refractive index (RI)

The lowest part of the tube ultracentrifuged by Example 2-(3) was perforated by an injection needle, and 3 to 6 drops per fraction of liquid flowing out of the tube were collected. When visible floating matter contaminated the fraction, the collection was stopped. The refractive index (RI) of each fraction was measured by a refractometer (manufactured by Reichert TECHNOLOGIES).

(5) Determination of Genomic Titer of Collected Fraction

The genomic titers of the fractions obtained by Example 2-(4) were determined in the same manner as Example 1-(6). Results are shown in Table 2 together with refractive indexes measured by Example 2-(4).

TABLE 2

| Fraction | Genomic titer ($\times 10^{11}$ VG/mL) | Total genomic titer ($\times 10^{11}$ VG) | Refractive index (RI) |
|---|---|---|---|
| 1 | 0.318 | 0.0636 | 1.3786 |
| 2 | 0.783 | 0.157 | 1.3765 |
| 3 | 3.62 | 0.725 | 1.3748 |
| 4 | 10.5 | 2.10 | 1.3735 |
| 5 | 20.0 | 3.99 | 1.3721 |
| 6 | 30.9 | 6.17 | 1.3713 |
| 7 | 29.3 | 5.86 | 1.3701 |
| 8 | 18.6 | 3.72 | 1.3689 |
| 9 | 21.3 | 4.26 | 1.3680 |
| 10 | 26.7 | 5.35 | 1.3667 |
| Before ultracentrifugation (Partially purified product) | 1.70 | 50.9 | — |

As seen from Table 2, the rAAV vector was accumulated in Fractions 4 to 10.

(6) Determination of Protein Purity in Collected Fraction

Fractions 5 to 10 obtained by Example 2-(4) in which more rAAV vector was accumulated were put in dialysis membranes (manufactured by Thermo Fisher Scientific Inc.), and dialyzed with PBS. To 10 μL of each fraction thus obtained, 10 μL of 2× sample buffer (manufactured by TAKARA BID Inc.) was added and mixed at 95° C. for 5 minutes. As a comparative control, the rAAV vector solution purified by the freeze-thaw method as described in Example 2-(1) was used. Each sample (10 μL) was applied onto 12.5% acrylamide gel (manufactured by ATTO Corp.) and electrophoresed. After termination of electrophoresis, the was immersed in a suitable amount of an Oriole fluorescent gel stain solution (manufactured by Bio-Rad Laboratories, Inc.), and shaken under light shielding for 90 minutes. After shaking, the gel was photographed with Luminoshot 400 (manufactured by TAKARA BIO Inc.). Results are shown in FIG. 1.

Figure 1:
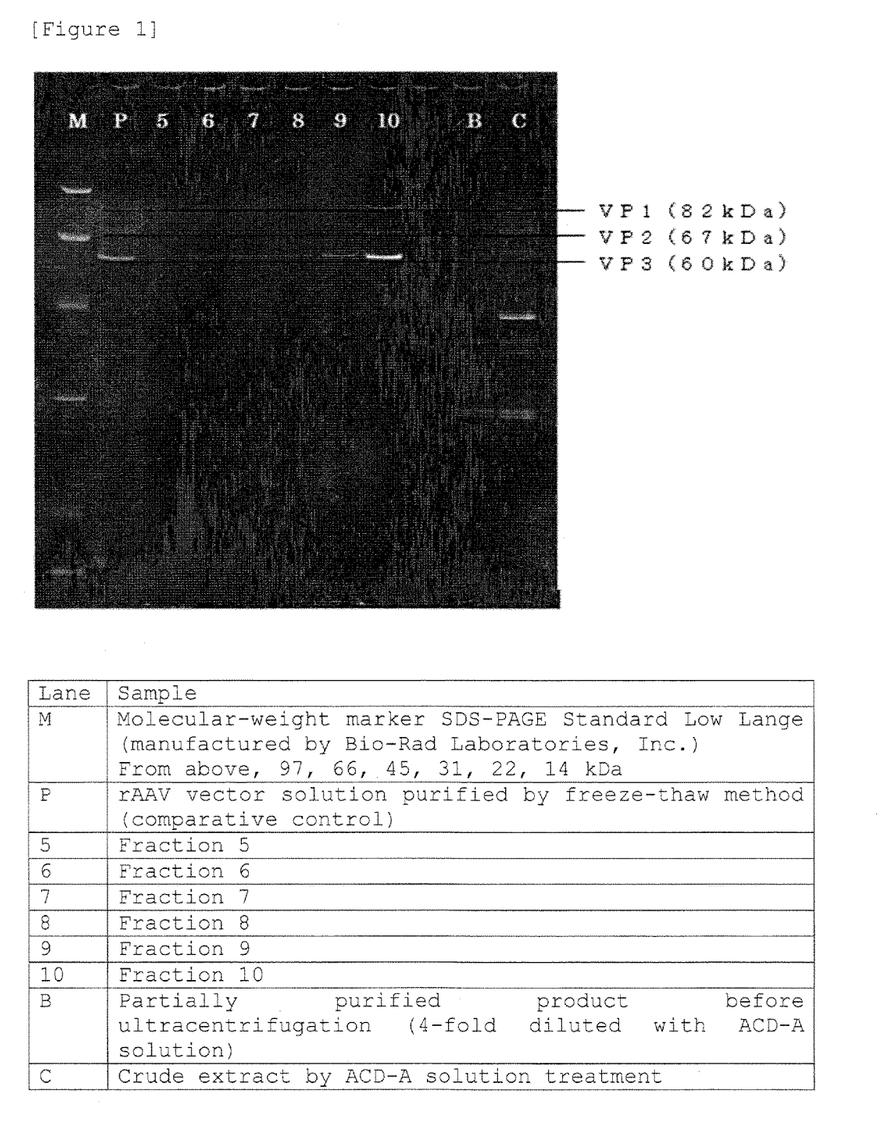
FIG. 1 A photograph showing fluorescence detection of a polyacrylamide gel in which ultracentrifugation-purified fractions are run in Example 2.

As seen from FIG. 1, in the case of using the purification method comprising the ADD-A solution treatment, the rAAV vector solutions (Fractions 5 to 10) after ultracentrifugation contained lower amounts of contaminating proteins and higher purity of the rAAV vector, as compared with the comparative control. As seen from Table 2, a recovery rate of the purification method comprising the ACD-A solution treatment was 57.7%, wherein the recovery rate is calculated by [(sum of total genomic titers of Fractions 5 to 10)×100]/total genomic titer before ultracentrifugation.

(7) Determination of Amount of Contaminating dsDNA in Collected Fraction

The amounts of dsDNA contained in the crude extract obtained by the ACD-A solution treatment in Example 2-(1), the partially purified product before ultracentrifugation obtained by Example 2-(2), Fraction 6 and Fraction 10 after dialysis obtained by Example 2-(6), and the rAAV vector solution purified by the freeze-thaw method in Example 2-(1) as a comparative control were determined according to a protocol described in PicoGreen dsDNA Quantitation Kit (manufactured by Invitrogen Inc.). Results are shown in Table 3.

TABLE 3

| Fraction | Amount of dsDNA (ng/mL) |
|---|---|
| Crude extract by ACD-A solution treatment | 2480.65 |
| Partially purified product before ultracentrifugation | 706.16 |
| Fraction 6 | 9.19 |
| Fraction 10 | 20.11 |
| rAAV vector solution purified by freeze-thaw method (Comparative control) | 61.34 |

As seen from the results of Table 3, despite the fact that Fraction 6 and Fraction 10 were not treated with BENZONASE before ultracentrifugation, the dsDNA amounts of Fraction 6 and Fraction 10, were lower than that of the comparative control (which was treated with BENZONASE). These results show that when a crude extract is obtained by treatment with the ACD-A solution and purified by ultracentrifugation, a rAAV vector solution with high purity is obtained as compared with a conventional method.

Example 3: Effect of Crude Extraction with Acidic Solution in Purification Step (Purification by Cation Exchange Chromatography)

(1) Preparation of Crude Extract for Chromatography

A partially purified product was prepared in the same manner as Example 2-(1) and (2). The partially purified product was 5-fold diluted with water for injection (manufactured by Otsuka Pharmaceutical Co., Ltd.), and the dilution was used as a sample to be applied.

(2) Purification by Cation Exchange Chromatography

A syringe (manufactured by TERUMO Corp.), a posidyne filter having pore size of 0.2 μm, and a cation exchange membrane (Mustang S; manufactured by Pall Corp.) were connected in this order to set up a cation exchange chromatography apparatus. The syringe was charged with 5 mL of the ACD-A solution that was 5-fold diluted with water for injection, and the solution was allowed to pass through the filter and membrane at a flow rate of about 4 mL/minute. Then, the syringe was exchanged, and 10 mL of the sample to be applied prepared by Example 3-(1) was allowed to pass through the apparatus in the same manner as described above. At this time, a penetrated liquid was collected as a flow-through fraction. The syringe was exchanged, and 5 mL of the ADD-A solution that was 5-fold diluted with water for injection was allowed to pass through the apparatus in the same manner as described above. At this time, a penetrated liquid was collected as a wash fraction. Further, the syringe was exchanged, and (1) 3 mL of a 50 mM glycine-sodium hydroxide buffer (pH 9), (2) 3 mL of PBS, and 3 mL of 2M NaCl were allowed to pass through the apparatus at the same flow rate as described above. At this time, a penetrated liquid was collected as (1) Eluate 1, (2) Eluate 2, or (3) Eluate 3.

(3) Determination of Genomic Titer in Each Fraction

The genomic titer of each fraction obtained by Example 3-(2) was determined in the same manner as Example 1-(6). Results are shown in Table 4.

TABLE 4

| Fraction | Total genomic titer (×10^9 VG) |
|---|---|
| Sample to be applied | 5.79 |
| Flow-through fraction | Below measurement limit |
| Wash fraction | Below measurement limit |
| Eluate 1 | 0.38 |
| Eluate 2 | 4.13 |
| Eluate 3 | 0.72 |

As seen from Table 4, the majority (71.3%) of the applied rAAV vectors were eluted into Eluate 2 (PBS).

(4) Determination of Protein Purity in Each Fraction

Each eluate obtained by Example 3-(2) was put in a dialysis membrane (manufactured by Thermo Fisher Scientific Inc.), and dialyzed with PBS. The protein purity was determined in the same manner as Example 2-(6). As a comparative control, the rAAV vector solution (Fraction 10) extracted with the acidic solution and then purified by ultracentrifugation in Example 2-(4) was subjected to determination of the protein purity in the same manner. Results are shown in FIG. 2.

Figure 2:
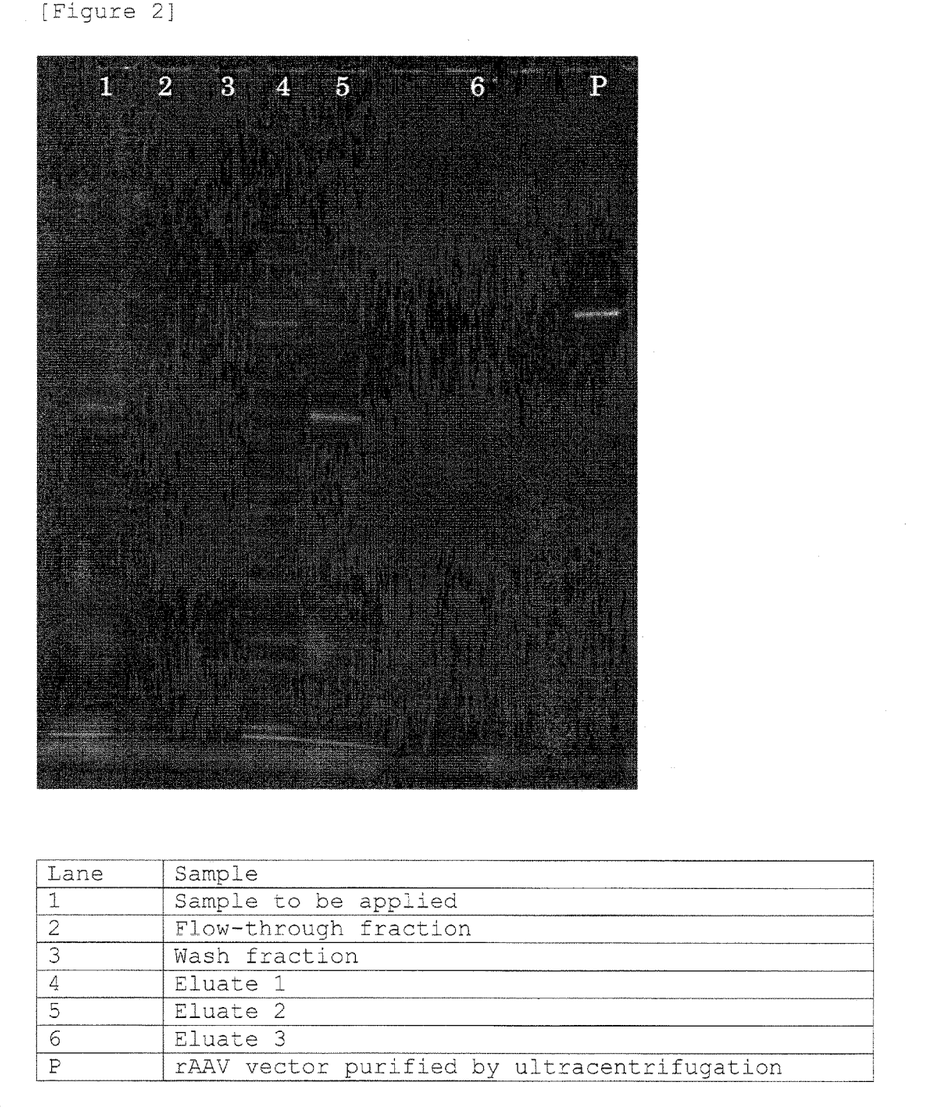
FIG. 2 A photograph showing fluorescence detection of a polyacrylamide gel in which cation exchange chromatography-purified fractions are run in Example 3.

As seen from FIG. 2, the majority of contaminating proteins were eluted into Eluate 1. As shown in Table 4, the rAAV vector was hardly detected in Eluate 1. These results show that the crude extract obtained by the ACD-A solution treatment can be subjected to purification by cation exchange column chromatography in the same manner as a conventional method, and the rAAV vector can be separated from the contaminating proteins by the cation exchange column chromatography apparatus.

Example 4: Study of Temperature for Acidic Solution Treatment (1) Collection of rAAV Vector-Producing Cell A rAAV vector-producing cell was collected in the same manner as Example 1-(1) to (3), except that a CellBIND (registered trademark) T75 flask (manufactured by Corning Inc.) was used as a culture vessel and associated reaction systems were scaled up.

(2) ACD-A Solution Treatment at Each Temperature

To the rAAV vector-producing cell obtained by Example 4-(1), 1 mL of the ACD-A solution was added, followed by mixing with a vortex mixer for 15 seconds. The mixture was left standing for 5 minutes at (1) 37° C., (2) 21° C., or (3) 4° C., again mixed by a vortex mixer for 15 seconds, and then centrifuged at 4° C. and 14,000×g for 10 minutes. A supernatant thus obtained was used as a crude extract.

(3) Determination of Genomic Titer of Crude Extract

The genomic titer of each crude extract obtained by Example 4-(2) was determined in the same manner as Example 1-(6). Results are shown in Table 5.

TABLE 5

| Treatment temperature | Genomic titer (×10^10 VG/mL) |
|---|---|
| 37° C. | 5.32 |
| 21° C. | 5.79 |
| 4° C. | 7.06 |

As seen from Table 5, there is no remarkable difference in the genomic titer of the crude extract among treatment temperature 37° C., 21° C., and 4° C. These results show that a rAAV vector can be extracted by treatment with the ACD-A solution at a wide range of temperature.

Example 5: Study of Crude Extraction in 293T Cell (1) Collection of rAAV Vector-Producing Cell A rAAV vector-producing cell was collected in the same manner as Example 4-(1), except that a 293T cell was used as a host.

(2) Preparation of Crude Extract

From the rAAV vector-producing cell obtained by Example 5-(1), crude extracts were obtained under three conditions as described below. Extraction by ultrasonic disruption was performed in the same manner as Example 1-(4). Extraction by treatment with the ACT-A solution was performed in the same manner as Example 1-(5). Extraction by freeze-thaw was performed by resuspending a cell pellet in 300 μL of PBS, and repeating a treatment consisting of "still standing in a dry ice-ethanol solution for 5 minutes, still standing in a water bath at 37° C. for 3 minutes, and mixing by a vortex mixer for 1 minute" three times to prepare a cell homogenate containing the rAAV vector. The cell homogenates thus obtained were centrifuged at 4° C. and 14,000×g for 20 minutes, and supernatants were collected. To the supernatants, 700 μL of PBS was added to prepare the crude extracts.

(3) Determination of Genomic Titer of Crude Extract

The genomic titer of each crude extract obtained by Example 5-(2) was determined in the same manner as Example 1-(6). Results are shown in Table 6.

TABLE 6

| Extraction condition | Genomic titer (×10^12 VG/mL) |
|---|---|
| Ultrasonic disruption | 1.53 |
| Freeze-thaw | 0.59 |
| ACD-A solution treatment | 2.26 |

As seen from Table 6, in the case of using the rAAV vector-producing cell prepared from the 293T cell, efficiency of extraction of the rAAV vector by the ACD-A solution treatment was 1.5 times higher than that of extraction by ultrasonic disruption, and 3.8 times higher than that of extraction by freeze-thaw.

Example 6: Study of Salt Concentration of Acidic Solution-1

(1) Preparation of Citrate Buffer Equivalent to ACD-A Solution, and Preparation of Citrate Buffer Having Each Salt Concentration A 38.1 mM citrate buffer (pH 4.9) containing 38.1 mM citric acid and 74.8 mM sodium citrate was prepared by reference to the package insert of the ACD-A solution. The citrate ion concentration of the citrate buffer was the same as that of the ACD-A solution. In addition, to the citrate buffer, sodium chloride was added at a final concentration of 50 mM or 200 mM. These buffers were used to obtain crude extracts.

(2) Preparation of Crude Extract with Each Acidic Solution

A rAAV vector-producing cell was collected in the same manner as Example 5-(1). To the collected cell, each buffer prepared by Example 6-(1) or the ACD-A solution was added. A crude extract was obtained in the same manner as Example 1-(5). As a comparative control, a crude extract was prepared by ultrasonic disruption in the same manner as Example 1-(4).

(3) Determination of Genomic Titer of Crude Extract

The genomic titer of each crude extract obtained by Example 6-(2) was determined in the same manner as Example 1-(6). Results are shown in Table 7.

TABLE 7

| Extraction condition | Sodium ion concentration (mM) | Genomic titer (×10^9 VG/mL) |
|---|---|---|
| ACD-A solution | 224 | 8.13 |
| citrate buffer | 224 | 6.13 |
| citrate buffer + 50 mM NaCl | 274 | 9.41 |
| citrate buffer + 200 mM NaCl | 424 | 14.4 |
| Ultrasonic disruption (Comparative control) | 161 | 2.78 |

As seen from Table 7, the crude extract with higher genomic titer was obtained by use of the acidic solution (ACD-A solution, or each citrate buffer) as compared with the genomic titer of the crude extract obtained by ultrasonic disruption (comparative control). When the sodium ion concentration in the citrate buffer was higher, the genomic titer of the obtained crude extract was higher. These results show that a rAAV vector can be effectively extracted by use of an acidic solution, and a higher sodium ion concentration in the acidic solution results in higher efficiency of extraction of the rAAV vector.

(4) Determination of Infectious Titer to HT1080 Cell Using Crude Extract

HT1080 cells were suspended at 5×10^4 cells/well in DMEM (manufactured by Sigma-Aldrich Co. LLC.) containing 10% FBS, and 1 mL of the suspension was seeded in a 24-well plate (manufactured by Corning Inc.), followed by cultivation at 37° C. in a $CO_2$ incubator. The next day, 2 of each crude extract containing the rAAV vector obtained by Example 6-(2) was added to each well to infect the cells. Two days later, trypLE Select (manufactured by Invitrogen Inc.) was used to disperse the cells. Then, the cell expressing fluorescent protein (AcGFP1) which was introduced into the cell by infection with the rAAV vector was detected using FACS CantoII (manufactured by Becton, Dickinson and Company). A rate (%) of AcGFP1 positive cells was calculated. The calculated value can be regarded as the infectious titer of the rAAV vector in each crude extract. Results are shown in Table 8.

TABLE 8

| Extraction condition | AcGFP1 positive cell rate (%) |
|---|---|
| ACD-A solution | 16.9 |
| citrate buffer | 12.7 |
| citrate buffer + 50 mM NaCl | 18.8 |
| citrate buffer + 200 mM NaCl | 24.3 |
| Ultrasonic disruption (Comparative control) | 6.4 |

As seen from Table 8, the crude extract with higher efficiency of infection of the rAAV vector was obtained by use of the acidic solution (ACD-A solution, or each citrate buffer) as compared with that of the crude extract obtained by ultrasonic disruption (comparative control). When the sodium ion concentration in the citrate buffer was higher, the infectious titer of the obtained crude extract was higher.

These results show that a rAAV vector can be effectively extracted by use of an acidic solution, and a higher sodium ion concentration in the acidic solution results in higher efficiency of extraction of the rAAV vector.

Example 7: Purification of rAAV Vector Using Heparin Column (1) Culture of rAAV Vector-Producing Cell A rAAV vector-producing cell was cultured in the same manner as Example 1-(1) to (2), except that a CellBIND (registered trademark) T225 flask (manufactured by Corning Inc.) was used as a culture vessel and associated reaction systems were scaled up.

(2) Preparation of Crude Extract with Each Acidic Solution

To the rAAV vector-producing cell after 48 hours from transfection, 0.5 M EDTA (pH 8.0) was added. After still standing for 10 minutes, the rAAV vector-producing cell was collected. The collected cell was centrifuged at 4° C. and 1,750×g for 10 minutes. After centrifugation, a supernatant was removed. Then, to the cell pellet, 2 mL of the citrate buffer+50 mM NaCl which was prepared by Example 6-(1) was added, followed by mixing with a vortex mixer. The mixture was left standing for 5 minutes, again mixed by a vortex mixer, and then centrifuged at 4° C. and 1,750×g for 10 minutes. A supernatant was collected. To the collected supernatant, a 1/13 amount of 2 M Tris-HCl (pH 9.5) was added for the purpose of neutralization, and then, a 1/100 amount of 1 M $MgCl_2$ was added to obtain a crude extract. To the cell pellet as described above, 2 mL of DMEM was added, followed by freeze-thaw using liquid nitrogen and a 37° C. water bath three times. A crude extract thus obtained was used as a comparative control.

(3) Preparation of Sample to be Applied

To each crude extract obtained by Example 7-(2), Cold-active Nuclease (manufactured by TAKARA BIG Inc.) was added at a final concentration of 0.2 units/μL, and maintained at 37° C. for 30 minutes for reaction. After reaction, the reaction mixture was centrifuged at 4° C. and 2,380×g for 10 minutes. A supernatant was collected. To the collected supernatant, a 1/10 amount of 5% sodium deoxycholate was added, and maintained at 37° C. for 30 minutes for reaction. After reaction, the reaction mixture was centrifuged at 4° C. and 2,380×g for 10 minutes. A supernatant was used as a sample to be applied.

(4) Purification by Heparin Resin Column Chromatography

To HisTALON Gravity Columns (manufactured by Clontech laboratories Inc.), 0.7 mL of heparin resin (manufactured by Nihon Pall Ltd.) 50% slurry was added to prepare a heparin resin column. Then, the heparin resin column was equilibrated with 3.5 mL of PBS, and 2.8 mL of the viral sample to be applied as described above was applied to the column. The resin was washed with 3.5 ml of PBS containing NaCl at a final concentration of 0.1 M. After washing, 1 mL of PBS containing NaCl at a final concentration of 0.4 M was allowed to pass through the column. At this time, a penetrated liquid was collected as an eluate containing the rAAV vector. The eluate containing the rAAV vector was added to an Amicon Ultra-0.5 centrifugal filter unit with Ultracel-100 membrane (manufactured by Merck Millipore Corp.), centrifuged at 4° C. and 2,000×g for 5 minutes, desalted, and concentrated. The same operations as described above were repeated. After all eluates were desalted and concentrated, the rAAV vector on the membrane was collected with 200 μL of PBS containing 0.5% sorbitol. The purity of the collected rAVV vector solution was confirmed by SDS-polyacrylamide gel electrophoresis. Results are shown in FIG. 3.

Figure 3:
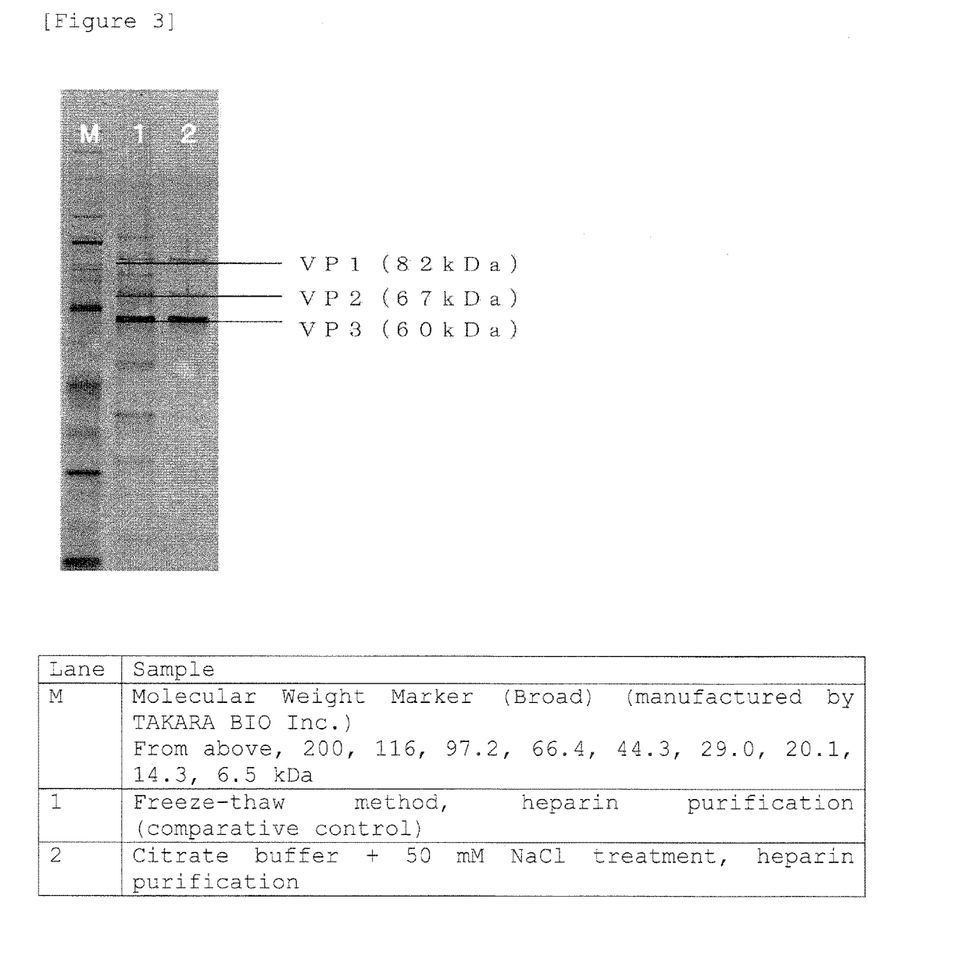
FIG. 3 A photograph showing fluorescence detection a polyacrylamide gel in which heparin column chromatography-purified fractions are run in Example 7.

As seen from FIG. 3, the heparin resin column chromatography-purified rAAV vector starting from the crude extract obtained by treatment with the citrate buffer+50 mM NaCl contained lower amounts of contaminating proteins and had higher purity of the rAAV vector, as compared with the comparative control.

Example 8: Study of Salt Concentration of Acidic Solution-2

(1) Preparation of Acidic Buffer

As a buffer to obtain a rAAV vector crude extract, a citrate buffer (pH 4.2) containing 53.4 mM citric acid and 53.4 mM sodium citrate was prepared. In addition, to this citrate buffer, sodium chloride was added at a final concentration of 200 mM, 400 mM, 600 mM, 800 mM, 1.0 M, 1.5 M, 2.0 M, or 2.5 M. These buffers were used to obtain crude extracts.

(2) Preparation of Crude Extract with Each Acidic Solution

A rAAV vector-producing cell was collected in the same manner as Example 5-(1). To the collected cell, each buffer prepared by Example 8-(1) or the ACD-A solution was added. A crude extract was obtained in the same manner as Example 1-(5).

(3) Determination of Genomic Titer of Crude Extract

The genomic titer of each crude extract obtained by Example 8-(2) was determined in the same manner as Example 1-(6). Results are shown in Table 9.

TABLE 9

| Extraction condition | Sodium ion concentration (mM) | Genomic titer ($\times 10^9$ VG/mL) |
|---|---|---|
| citrate buffer | 160.2 | 13.2 |
| citrate buffer + 200 mM NaCl | 360.2 | 11.3 |
| citrate buffer + 400 mM NaCl | 560.2 | 21.2 |
| citrate buffer + 600 mM NaCl | 760.2 | 36.8 |
| citrate buffer + 800 mM NaCl | 960.2 | 41.4 |
| citrate buffer + 1.0M NaCl | 1160.2 | 35.8 |
| citrate buffer + 1.5M NaCl | 1660.2 | 34.4 |
| citrate buffer + 2.0M NaCl | 2160.2 | 30.7 |
| citrate buffer + 2.5M NaCl | 2660.2 | 26.2 |

As seen from Table 9, when the sodium ion concentration of the citrate buffer was higher (in particular, a range of 760 to 1660 mM), the genomic titer of the obtained crude extract was higher. These results show that about 0.6 to 2 M of sodium ion concentration in an acidic solution increases efficiency of extraction of a rAAV vector.

Example 9: Removal of Contaminating Protein by Addition of Citric Acid-1

(1) Preparation of Crude Extract with Citrate Buffer

A rAAV vector-containing crude extract was obtained in the same manner as Example 6-(2), except that a citrate buffer 200 mM NaCl prepared by the method described in Example 6-(1) was used as an extraction buffer.

(2) Citric Acid-Precipitation

To the rAAV vector-containing crude extract obtained by Example 9-(1), a 1/10 amount of a 1 M citric acid solution was added and well suspended, followed by still standing at 4° C. for 60 minutes. After still standing, the suspension was centrifuged at 4° C. and 1,750×g for 20 minutes. A supernatant was collected to obtain a solution after citric acid-precipitation.

(3) Determination of Genomic Titer and Protein Concentration (A280) Before and after Citric Acid-Precipitation The genomic titer and the protein concentration (A280) of the crude extract and the solution after citric acid-precipitation were determined in the same manner as Example 1-(6). Results are shown in Table 10.

TABLE 10

|  | Genomic titer (×10^12 VG/mL) | A 280 measurement |
|---|---|---|
| Crude extract | 2.25 | 4.92 |
| solution after citric acid-precipitation | 2.41 | 2.22 |

As seen from Table 10, the genomic titer hardly changed between before and after citric acid-precipitation. After citric acid-precipitation, the protein concentration (A280) decreased. These results show that when a crude extract obtained by treatment with an acidic solution is subjected to citric acid-precipitation, a rAAV vector solution with high purity is obtained.

Example 10: Removal of Contaminating Protein by Addition of Citric Acid-2

(1) Preparation of Crude Extract with Each Acidic Solution

A rAAV vector-containing crude extract was obtained in the same manner as Example 6-(2), except that a "citrate buffer+200 mM NaCl ((i) and (ii))" or a "citrate buffer+200 mM NaCl, further containing a 1/10 amount of 1 M citric acid ((iii))" was used as an extraction buffer, wherein the "citrate buffer+200 mM NaCl" was prepared by the method described in Example 6-(1). As a comparative control, a crude extract was prepared by ultrasonic disruption in the same manner as Example 1-(4) ((iv)).

(2) Citric Acid-Precipitation

A part of each of the crude extracts (i) to (iv) obtained by Example 10-(1) was taken out, and designated Before solutions (i) to (iv) To the rest of crude extract (ii), a 1/10 amount of 1 M citric acid solution was added and well suspended, followed by still standing at 4° C. for 60 minutes. On the other hand, to the rest of each of crude extract (i), crude extract (iii) and crude extract (iv), a 1/10 amount of the extraction buffer used for their extraction was added and well suspended, followed by still standing at 4° C. for 60 minutes. After still standing, each suspension was centrifuged at 4° C. and 1,750×g for 20 minutes and a supernatant was collected. The supernatants were designated After solutions (i) to (iv).

Figure 41:
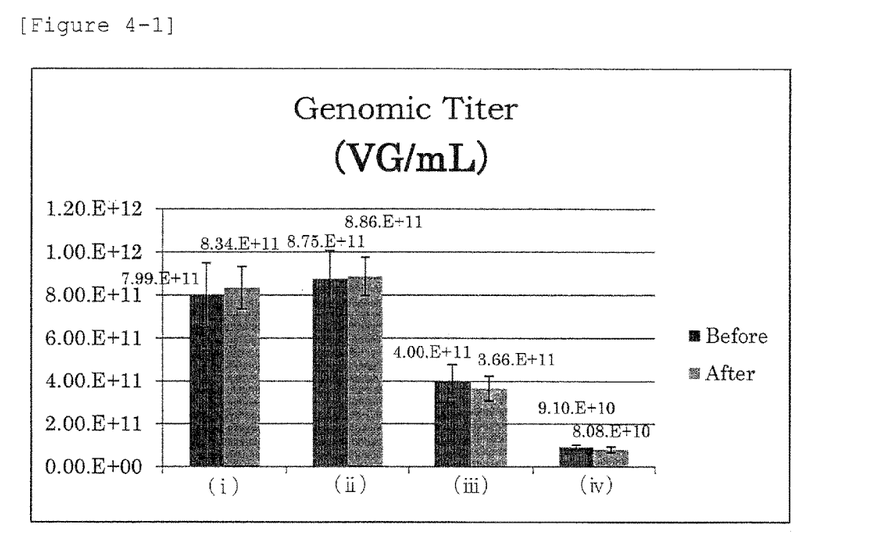
Figure 42:
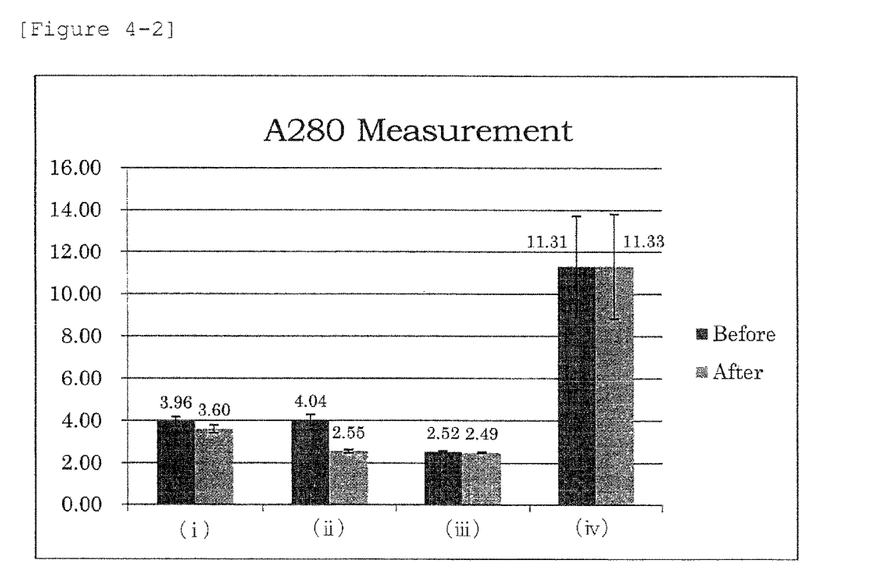
Figure 43:
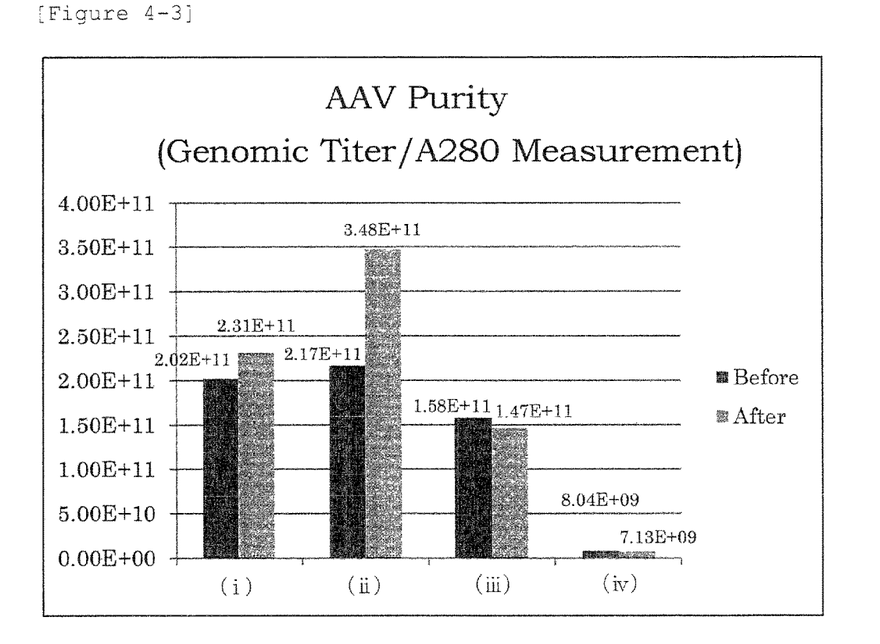

(3) Determination of Genomic Titer, Determination of Protein Concentration (A280), and Calculation of AAV Purity The genomic titer and the protein concentration (A280) of Before solutions (i) to (iv) and After solutions (i) to (iv) were determined in the same manner as Example 1-(6). In addition, the AAV purity was calculated by "genomic titer/A280 measurement". Results are shown in FIG. 4-1 to FIG. 4-3.

As seen from FIG. 4-3, the AAV purity of After solution (ii) was the highest. This shows that when a crude extract obtained by treatment with an acidic solution is subjected to citric acid-precipitation, a rAAV vector solution with high purity is obtained.

INDUSTRIAL APPLICABILITY

According to the method of producing a non-enveloped virus of the present invention, a solution containing a non-enveloped virus with high purity can be efficiently obtained without laborious operations. A non-enveloped virus produced by the method of the present invention and a composition comprising the non-enveloped virus as an active ingredient are very useful in gene transfer methods in the fields of basic research study and clinical application for gene therapy.

The invention claimed is:

1. A method of producing a non-enveloped virus, the method comprising:
    (a) culturing an isolated cell, wherein a non-enveloped virus is replicating within said cell,
    (b) removing the culture solution or media from the cell,
    (c) bringing the cell into contact with an acidic solution, and
    (d) isolating the non-enveloped virus from the cell and acidic solution mixture of step (c),
    wherein the non-enveloped virus is an adeno-associated virus, and wherein the acidic solution is at pH 3.0-6.9.
2. The method according to claim 1, wherein the acidic solution contains a sodium ion and/or a potassium ion.
3. The method according to claim 1, wherein the virus is further purified after isolation in step (d).
4. The method according to claim 3, wherein the purification of the non-enveloped virus is performed by an operation selected from ultracentrifugation, chromatography, and ultrafiltration.
5. The method according to claim 1, wherein the acidic solution contains a cation and citric acid.
6. The method according to claim 1, wherein the isolation of step (d) is performed via centrifugation or filtration.
7. The method according to claim 1, which does not comprise a physical cell disruption method.

* * * * *